United States Patent [19]

Annen et al.

[11] 4,432,976
[45] Feb. 21, 1984

[54] CYCLOCARBONATE ESTERS OF 16α,17α, DIHYDROXY ANTI-INFLAMMATORY STEROIDS

[75] Inventors: Klaus Annen; Henry Laurent; Helmut Hofmeister, all of Berlin, Fed. Rep. of Germany

[73] Assignee: Schering Aktiengesellschaft, Berlin and Bergkamen, Fed. Rep. of Germany

[21] Appl. No.: 410,756

[22] Filed: Aug. 23, 1982

[30] Foreign Application Priority Data

Aug. 21, 1981 [DE] Fed. Rep. of Germany ....... 3133631

[51] Int. Cl.³ ............................................. A61K 31/58
[52] U.S. Cl. ........................ 424/241; 260/239.55 R; 260/239.57
[58] Field of Search ............. 260/239.55 D, 239.55 R, 260/239.57; 424/241

[56]  References Cited

U.S. PATENT DOCUMENTS

| 2,990,401 | 6/1961 | Bernstein et al. | 260/239.55 D |
| 3,050,519 | 8/1962 | Fried | 260/239.55 R |
| 3,357,974 | 12/1967 | Taub | 260/239.55 D |
| 3,971,772 | 7/1976 | Cimarusti et al. | 260/239.55 R |
| 3,971,773 | 7/1976 | Cimarusti et al. | 260/239.55 R |

Primary Examiner—Elbert L. Roberts
Attorney, Agent, or Firm—Millen & White

[57]  ABSTRACT

Corticoids of Formula I

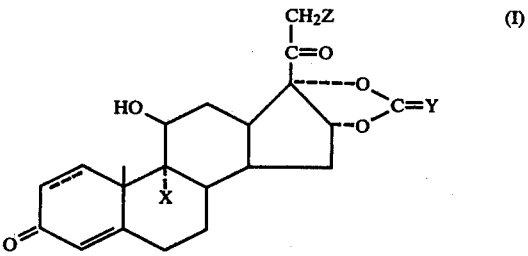

wherein
 is a single bond or a double bond,
X is hydrogen, fluorine, or chlorine,
Y represents two hydrogen atoms or an oxygen atom, and
Z is hydrogen or acyloxy of 2-6 carbon atoms, are pharmacologically active compounds, e.g., as anti-inflammatories.

14 Claims, No Drawings

CYCLOCARBONATE ESTERS OF 16α,17α, DIHYDROXY ANTI-INFLAMMATORY STEROIDS

This invention relates to new corticoid derivatives.

SUMMARY OF THE INVENTION

It is an object of this invention to provide new corticoids having valuable pharmacological properties.

Upon further study of the specification and appended claims, further objects and advantages of this invention will become apparent to those skilled in the art.

These objects have been attained by providing new corticoids of the Formula I

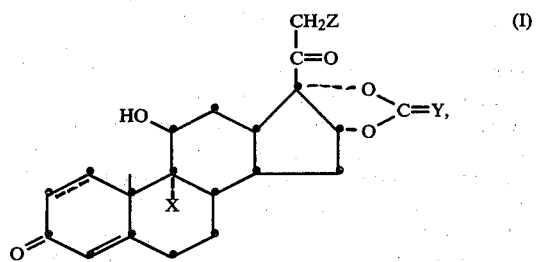

wherein
- - - - is a single bond or a double bond,
X is hydrogen, fluorine, or chlorine,
Y represents two hydrogen atoms or an oxygen atom, and
Z is hydrogen or acyloxy of 2–6 carbon atoms.

DETAILED DISCUSSION

The novel corticoids of Formula I can carry, as the acyloxy group Z of 2–6 carbon atoms, for example acetoxy, propionyloxy, butyryloxy, isobutyryloxy, valeryloxy, 3-methylbutyryloxy, trimethylacetoxy, hexanoyloxy, etc., i.e., especially, alkanoyloxy.

The corticoids of this invention possess, upon topical administration, a strongly antiinflammatory activity and have a relatively weak efficacy upon systemic administration.

Accordingly, a novel corticoids of Formula I are suitable in combination with the excipients customary in galenic pharmacy for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin disorders.

The drug specialties are prepared as usual by converting the active agents with suitable additives into the desired form of administration, such as, for example: solutions, lotions, ointments, creams, or plasters. In the thus-formulated medicines, the active agent concentration is dependent on the form of administration. With lotions and ointments, an active agent concentration of 0.001–1% is preferably employed.

Moreover, the novel compounds, optionally in combination with the usual excipients and auxiliary agents, are also well suited for the preparation of inhalants usable for the therapy of allergic diseases of the respiratory tract, e.g. bronchial asthma or rhinitis.

The novel corticoids are furthermore also suitable, in the form of capsules, tablets, or dragees containing preferably 10–200 mg of active agent and administered orally, or in the form of suspensions preferably containing 100–500 mg of active agent per dosage unit and administered rectally, for the treatment of allergic diseases of the intestinal tract, such as colitis ulcerosa and colitis granulomatosa.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For topical application, the compounds can be employed as non-sprayable forms, viscous to semi-solid or solid forms comprising a carrier indigenous to topical application and having a dynamic viscosity preferably greater than water. Suitable formulations include but are not limited to solutions, suspensions, lotions, emulsions, creams, ointments, plasters, powders, linaments, salves, aerosols, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

In the thus-formulated medicinal agents, the effective agent concentration is dependent on the compound used and the form of application and can be easily determined by clinical tests under conventional considerations. Usually, the active compounds of the invention are incorporated in topical formulations in a preferred concentration of about 0.001 to 1 wt. %.

The method and repetition of administration will vary with the particular form of administration and the indication involved, but will normally be from 1 to 10 times daily.

Unless otherwise indicated herein, administration of the compounds of this invention will be analogous to that of known topical antiinflammatories such as triamcinolone acetonide (J. Am. Chem. Soc. 81, 1959,1689).

The novel corticoids can be prepared according to known processes, e.g., by (a) condensing a corticoid of Formula II

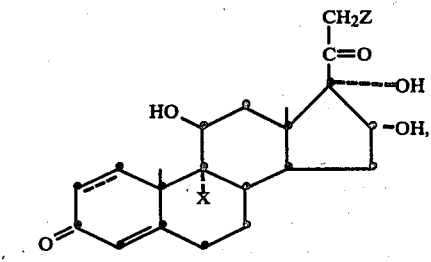

wherein ---, X and Z are as defined above, with a compound of Formula III

wherein Y' is an oxygen atom and R' is alkyl of 1–4 carbon atoms; or (b) chemically adding hypochlorous or hypobromous acid to the $\Delta^{9(11)}$-double bond of a corticoid of Formula IV

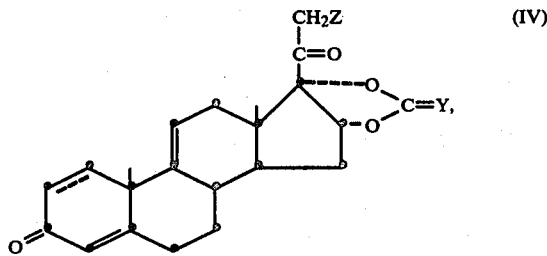

wherein ---, Y and Z are as defined above, and optionally eliminating the 9-halogen atom or converting the 11β-hydroxy-9-halogen compound into the 9,11β-epoxide, and opening up the latter with hydrogen fluoride or hydrogen chloride; or optionally hydrogenating the $\Delta^{1,4}$-corticoids of Formula I obtained according to process version (a) or (b) to the corresponding $\Delta^4$-corticoids; or saponifying 21-acetyl compounds wherein Y means two hydrogen atoms to the corresponding 21-hydroxy compounds; or esterifying or converting 21-hydroxy steroids of Formula I into the 21-chloro compounds.

These processes can all be conducted using fully conventional methods.

All starting materials are either known or preparable using fully conventional methods and available materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) Under agitation at room temperature, a mixture of 54.6 g of kieselguhr W 20 and 27.3 g of phosphorus pentoxide is added in incremental portions to a solution of 34.4 g of 21-acetoxy-16α,17α-dihydroxy-1,4,9-pregnatriene-3,20-dione in 254 ml of anhydrous methylene chloride and 164 ml of anhydrous formaldehyde dimethylacetal. The mixture is stirred for another hour, vacuum-filtered, the residue washed with triethylamine-containing methylene chloride, and the filtrate is concentrated to dryness under vacuum. The crude product is purified on 3.5 kg of silica gel with a methylene chloride-acetone gradient (0–12% acetone). Yield: 29.7 g of 21-acetoxy-16α,17α-methylenedioxy-1,4,9-pregnatriene-3,20-dione, mp 200° C.

(b) A solution of 12.0 g of 21-acetoxy-16α,17α-methylenedioxy-1,4,9-pregnatriene-3,20-dione in 120 ml of dioxane is combined at room temperature under agitation with 11.28 g of N-bromosuccinimide. To this mixture is added dropwise 60 ml of a 10% aqueous perchloric acid solution; the mixture is stirred for 10 minutes at room temperature and poured on an ice water-sodium chloride solution. After the mixture has been worked up as usual, 16.6 g of 21-acetoxy-9α-bromo-11β-hydroxy-16α,17α-methylenedioxy-1,4-pregnadiene-3,20-dione is obtained; this product is recrystallized from acetone/hexane; mp 188° C.

(c) A solution of 10.2 g of 21-acetoxy-9α-bromo-11β-hydroxy-16α,17α-methylenedioxy-1,4-pregnadiene-3,20-dione in 210 ml of tetrahydrofuran is refluxed for one hour with 72.25 ml of tri-n-butyltin hydride and a spatula tip of azobisisobutyronitrile. After the reaction solution has been concentrated to dryness under vacuum, the residue is purified on 1.1 kg of silica gel by eluting first with 5 l of hexane and then with a methylene chloride-acetone gradient (0–15% acetone). Yield: 7.9 g of 21-acetoxy-11β-hydroxy-16α,17α-methylenedioxy-1,4-pregnadiene-3,20-dione, mp 271° C. (decomposition).

EXAMPLE 2

1.5 g of 21-acetoxy-11β-hydroxy-16α,17α-methylenedioxy-1,4-pregnadiene-3,20-dione is dissolved in 510 ml of methanol and 111 ml of water and refluxed under agitation with 1.5 g of calcium carbonate for 24 hours. The calcium carbonate is removed by vacuum-filtering; the filtrate is concentrated to turbidity and poured on water. After the usual working-up process, the crude product is purified on 115 g of silica gel with a methylene chloride-acetone gradient (0–20% acetone), thus isolating 758 mg of 11β,21-dihydroxy-16α,17α-methylenedioxy-1,4-pregnadiene-3,20-dione, mp 220°–223° C. (decomposition).

EXAMPLE 3

A solution of 2.4 g of 11β,21-dihydroxy-16α,17α-methylenedioxy-1,4-pregnadiene-3,20-dione in 24 ml of pyridine and 12 ml of propionic acid anhydride is stirred for one hour at room temperature. After precipitation into ice water-sodium chloride, the mixture is filtered off and worked up as usual. The crude product is purified on 220 g of silica gel with a methylene chloride-acetone gradient (0–12% acetone), thus obtaining 2.5 g of 11β-hydroxy-16α,17α-methylenedioxy-21-propionyloxy-1,4-pregnadiene-3,20-dione, mp 184°–185° C.

EXAMPLE 4

Analogously to Example 3, 2.4 g of 11β,21-dihydroxy-16α,17α-methylenedioxy-1,4-pregnadiene-3,20-dione is reacted with butyric anhydride, worked up, and purified, thus isolating 2.6 g of 21-butyryloxy-11β-hydroxy-16α,17α-methylenedioxy-1,4-pregnadiene-3,20-dione, mp 140°–141° C.

EXAMPLE 5

Analogously to Example 3, 2.2 g of 11β,21-dihydroxy-16α,17α-methylenedioxy-1,4-pregnadiene-3,20-dione is reacted with n-valeric acid anhydride, worked up, and purified, thus obtaining 2.1 g of 11β-hydroxy-16α,17α-methylenedioxy-21-valeryloxy-1,4-pregnadiene-3,20-dione, mp 121°–122° C.

EXAMPLE 6

A suspension of 4.2 g of tris(triphenylphosphine)-rhodium(I) chloride in 195 ml of benzene and 65 ml of methanol is prehydrogenated for one hour at room temperature under normal pressure. Then 5.2 g of 21-acetoxy-11β-hydroxy-16α,17α-methylenedioxy-1,4-pregnadiene-3,20-dione in 195 ml of benzene and 65 ml of methanol is added thereto, and hydrogenation of the mixture is continued for 5 hours under normal pressure. The reaction solution is concentrated to dryness under vacuum, and the residue is purified on 1 kg of silica gel with a hexane-ethyl acetate gradient (0–60% ethyl acetate). Yield: 3.8 g of 21-acetoxy-11β-hydroxy-16α,17α-methylenedioxy-4-pregnene-3,20-dione, mp 241°–243° C.

EXAMPLE 7

(a) A suspension of 3.0 g of 21-acetoxy-9α-bromo-11β-hydroxy-16α,17α-methylenedioxy-1,4-pregnadiene-3,20-dione in 180 ml of ethanol is refluxed for 2½ hours with 4.2 g of potassium acetate. The mixture is concentrated, and poured on an ice water-sodium chloride solution. After the residue has been filtered off and washed, it is worked up as usual, and the crude product is purified on 220 g of silica gel with a methylene chloride-acetone gradient (0–15% acetone). Yield: 1.83 g of 21-acetoxy-9β,11β-epoxy-16α,17α-methylenedioxy-1,4-pregnadiene-3,20-dione, mp 168°–169° C.

(b) 1.5 ml of a 70% HF/pyridine solution is cooled to −35° C. and combined with 400 mg of 21-acetoxy-9β,11β-epoxy-16α,17α-methylenedioxy-1,4-pregnadiene-3,20-dione. The reaction mixture is stirred at −5° C. for 8 hours and then poured on ammoniacal ice water, filtered off, the residue washed neutral, and worked up as usual. The crude product is purified on 65 g of silica gel with a methylene chloride-acetone gradient (0–15% acetone), thus isolating 377 mg of 21-acetoxy-9α-fluoro-11β-hydroxy-16α,17α-methylenedioxy-1,4-pregnadiene-3,20-dione, mp 283°–285° C.

EXAMPLE 8

18.0 g of 21-acetoxy-9α-fluoro-11β-hydroxy-16α,17α-methylenedioxy-1,4-pregnadiene-3,20-dione is stirred in a mixture of 216 ml of 60% perchloric acid and 720 ml of methanol at room temperature for 18 hours. The reaction solution is diluted with methylene chloride and poured on water. After extraction with methylene chloride, neutralizing, washing, drying, and concentration of the organic extracts, 14.0 g of a crude product is obtained which is recrystallized from hexane/acetone, yielding 10.6 g of 9α-fluoro-11β,21-dihydroxy-16α,17α-methylenedioxy-1,4-pregnadiene-3,20-dione, mp 262° C.

EXAMPLE 9

(a) A solution of 2.0 g of 9α-fluoro-11β,21-dihydroxy-16α,17α-methylenedioxy-1,4-pregnadiene-3,20-dione in 20 ml of pyridine is stirred for one hour at room temperature with 2.4 g of tosyl chloride and poured on an ice water-sodium chloride solution. After working up the reaction mixture as usual, 2.4 g of 9α-fluoro-11β-hydroxy-16α,17α-methylenedioxy-21-tosyloxy-1,4-pregnadiene-3,20-dione is isolated.

(b) 2.4 g of 9α-fluoro-11β-hydroxy-16α,17α-methylenedioxy-21-tosyloxy-1,4-pregnadiene-3,20-dione is suspended in 48 ml of hexamethylphosphoric triamide and stirred with 2.4 g of lithium chloride for 2½ hours at 80° C. The mixture is poured on an ice water-sodium chloride solution, filtered off, and the residue is worked up as usual. The crude product is purified on 190 g of silica gel with a methylene chloride-acetone gradient (0–15% acetone). Yield: 1.2 g of 21-chloro-9α-fluoro-11β-hydroxy-16α,17α-methylenedioxy-1,4-pregnadiene-3,20-dione, mp 264°–265° C.

EXAMPLE 10

Under the conditions of Example 6, 3.2 g of 21-acetoxy-9α-fluoro-11β-hydroxy-16α,17α-methylenedioxy-1,4-pregnadiene-3,20-dione is hydrogenated and worked up. The product is purified on 350 g of silica gel with a hexane-ethyl acetate gradient (0–80% ethyl acetate), thus isolating 2.6 g of 21-acetoxy-9α-fluoro-11β-hydroxy-16α,17α-methylenedioxy-4-pregnene-3,20-dione, mp 264°–266° C.

EXAMPLE 11

A solution of 2.0 g of 21-acetoxy-16α,17α-methylenedioxy-1,4,9-pregnatriene-3,20-dione in 20 ml of dioxane is combined with 1.88 g of N-chlorosuccinimide and, under agitation, 10 ml of a 10% aqueous perchloric acid solution is added dropwise thereto. The reaction solution is stirred at room temperature for 2½ hours and then poured on an ice water-sodium chloride solution. The precipitate is filtered off, washed, and worked up as usual. The crude product is purified on 200 g of silica gel with a methylene chloride-acetone gradient (0–15% acetone), yielding 1.39 g of 21-acetoxy-9α-chloro-11β-hydroxy-16α,17α-methylenedioxy-1,4-pregnadiene-3,20-dione, mp 244°–245° C.

EXAMPLE 12

(a) Analogously to Example 6, 6.0 g of 21-acetoxy-16α,17α-methylenedioxy-1,4,9-pregnatriene-3,20-dione is hydrogenated over tris(triphenylphosphine)rhodium(I) chloride, worked up, and purified, thus isolating 5.4 g of 21-acetoxy-16α,17α-methylenedioxy-4,9-pregnadiene-3,20-dione, mp 201°–202° C.

(b) Under the conditions of Example 11, 2.0 g of 21-acetoxy-16α,17α-methylenedioxy-4,9-pregnadiene-3,20-dione is reacted with N-chlorosuccinimide, worked up, and purified, thus isolating 920 mg of 21-acetoxy-9α-chloro-11β-hydroxy-16α,17α-methylenedioxy-4-pregnene-3,20-dione, mp 231° C.

EXAMPLE 13

At 0° C., a solution of 6.0 g of 21-acetoxy-11β,16α,17α-trihydroxy-1,4-pregnadiene-3,20-dione in 60 ml of pyridine is combined dropwise with 4.5 ml of ethyl chloroformate and further stirred for 30 minutes. The reaction solution is poured on an ice water-sodium chloride solution, the precipitate is filtered off and, after washing, worked up as usual. The crude product is purified on 750 g of silica gel with a methylene chloride-acetone gradient (0–20% acetone). Yield: 4.76 g of 21-acetoxy-11β-hydroxy-1,4-pregnadieno[16α,17α-d]-[1,3]dioxolane-2′,3,20-trione, mp 250°–251° C.

EXAMPLE 14

Under the conditions of Example 6, 1.5 g of 21-acetoxy-11β-hydroxy-1,4-pregnadieno[16α,17α-d]-[1,3]dioxolane-2′,3,20-trione is hydrogenated and worked up. The crude product is purified on 200 g of silica gel with a methylene chloride-acetone gradient (0–15% acetone), thus isolating 1.1 g of 21-acetoxy-11β-hydroxy-4-pregneno[16α,17α-d]-[1,3]dioxolane-2′,3,20-trione, mp 232°–234° C.

EXAMPLE 15

(a) 2.5 g of 21-acetoxy-16α,17α-dihydroxy-1,4,9-pregnatriene-3,20-dione in 25 ml of pyridine is reacted with 1.9 ml of ethyl chloroformate analogously to Example 13, worked up, and purified. Yield: 1.93 g of 21-acetoxy-1,4,9-pregnatrieno[16α,17α-d]-[1,3]dioxolane-2′,3,20-trione, mp 204°–206° C.

(b) 1.2 g of 21-acetoxy-1,4,9-pregnatrieno-[16α,17α-d]-[1,3]dioxolane-2′,3,20-trione is reacted analogously to Example 11 with N-chlorosuccinimide, worked up, and purified, thus obtaining 595 mg of 21-acetoxy-9α-chloro-11β-hydroxy-1,4-pregnadieno[16α,17α-d]-[1,3]dioxolane-2′,3,20-trione, mp 247°–248° C.

EXAMPLE 16

1.0 g of 21-acetoxy-9α-chloro-11β-hydroxy-1,4-pregnadieno[16α,17α-d]-[1,3]dioxolane-2′,3,20-trione is combined in 50 ml of methylene chloride and 850 ml of methanol with a mixture of 100 ml of water and 200 ml of concentrated hydrochloric acid and stirred for 15 hours at room temperature. The reaction solution is neutralized with soda solution, concentrated, and poured on ice water, thus isolating 500 mg of 9α-chloro-11β,21-dihydroxy-1,4-pregnadieno[16α,17α-d]-[1,3]dioxolane-2′,3,20-trione, which is crystallized from hexane/acetone, mp 300° C.

EXAMPLE 17

(a) Analogously to Example 6, 6.0 g of 21-acetoxy-1,4,9-pregnatrieno[16α,17α-d]-[1,3]dioxolane-2′,3,20-trione is hydrogenated, worked up, and purified, thus isolating 5.1 g of 21-acetoxy-4,9-pregnadieno[16α,17α-d]-[1,3]dioxolane-2′,3,20-trione, mp 221°–223° C.

(b) Under the conditions of Example 12, 2.0 g of 21-acetoxy-4,9-pregnadieno[16α,17α-d]-[1,3]dioxolane-2′,3,20-trione is reacted with 1.9 g of N-chlorosuccinimide, worked up, and purified. Yield: 700 mg of 21-acetoxy-9α-chloro-11β-hydroxy-4-pregneno[16α,17α-d]-[1,3]dioxolane-2′,3,20-trione, mp 217°–218° C.

EXAMPLE 18

(a) A suspension of 6.0 g of 16α,17α-dihydroxy-21-propionyloxy-4,9-pregnadiene-3,20-dione in pyridine is reacted analogously to Example 15(a) with ethyl chloroformate, worked up, and purified, thus isolating 5.5 g of 21-propionyloxy-4,9-pregnadieno[16α,17α-d]-[1,3]dioxolane-2′,3,20-trione, mp 177°–178° C.

(b) 3.2 g of 21-propionyloxy-4,9-pregnadieno[16α,1-7α-d]-[1,3]dioxolane-2′,3,20-trione is reacted analogously to Example 12 with N-chlorosuccinimide, worked up, and chromatographed. Yield: 1.62 g of 9α-chloro-11β-hydroxy-21-propionyloxy-4-pregneno[16α,17α-d]-[1,3]dioxolane-2′,3,20-trione, mp 222°–223° C.

EXAMPLE 19

(a) 8.6 g of 21-butyryloxy-16α,17α-dihydroxy-4,9-pregnadiene-3,20-dione in 100 ml of pyridine is reacted under the conditions of Example 15(a) with 5.6 ml of ethyl chloroformate, worked up, and purified, thus isolating 7.9 g of 21-butyryloxy-4,9-pregnadieno[16α,1-7α-d]-[1,3]dioxolane-2′,3,20-trione, mp 178°–179° C.

(b) 7.5 g of 21-butyryloxy-4,9-pregnadieno[16α,17α-d]-[1,3]dioxolane-2′,3,20-trione is reacted as described in Example 12 with 7.0 g of N-chlorosuccinimide, worked up, and purified, thus obtaining 3.1 g of 21-butyryloxy-9α-chloro-11β-hydroxy-4-pregneno[16α,1-7α-d]-[1,3]dioxolane-2′,3,20-trione, mp 241°–242° C.

EXAMPLE 20

Under the conditions of Example 13, 1.5 g of 21-acetoxy-9α-fluoro-11β,16α,17α-trihydroxy-1,4-pregnadiene-3,20-dione is reacted with ethyl chloroformate and worked up. The crude product is purified by crystallization from acetone/hexane. Yield: 1.1 g of 21-acetoxy-9α-fluoro-11β-hydroxy-1,4-pregnadieno[16α,17α-d]-[1,3]dioxolane-2′,3,20-trione, mp 204°–205° C.

The preceding examples can be repeated with similar success by substituting the generically or specifically described reactants and/or operation conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A corticoid of the formula

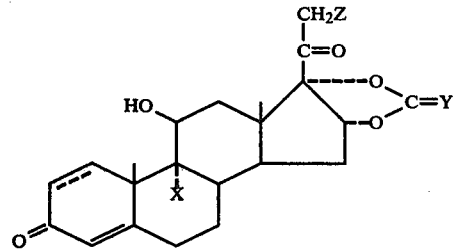

wherein

≈≈≈ is a single bond or a double bond,
X is hydrogen, fluorine, or chlorine,
Y represents an oxygen atom, and
Z is hydrogen or alkanoyloxy of 2–6 carbon atoms.

2. 21-Chloro-9α-fluoro-11β-hydroxy-16α,17α-methylenedioxy-1,4-pregnadiene-3,20-dione.

3. 21-Acetoxy-11β-hydroxy-1,4-pregnadieno[16α,1-7α-d]-[1,3]dioxolane-2′,3,20-trione, a compound of claim 1.

4. 21-Acetoxy-11β-hydroxy-4-pregneno[16α,17α-d]-[1,3]dioxolane-2′,3,20-trione, a compound of claim 1.

5. 21-Acetoxy-9α-chloro-11β-hydroxy-1,4-pregnadieno[16α,17α-d]-[1,3]dioxolane-2′,3,20-trione, a compound of claim 1.

6. 9α-Chloro-11β,21-dihydroxy-1,4-pregnadieno[16α,17α-d]-[1,3]dioxolane-2′,3,20-trione, a compound of claim 1.

7. 21-Acetoxy-9α-chloro-11β-hydroxy-4-pregneno[16α,17α-d]-[1,3]dioxolane-2′,3,20-trione, a compound of claim 1.

8. 9α-Chloro-11β-hydroxy-21-propionyloxy-4-pregneno[16α,17α-d]-[1,3]dioxolane-2′,3,20-trione, a compound of claim 1.

9. 21-Butyryloxy-9α-chloro-11β-hydroxy-4-pregneno[16α,17α-d]-[1,3]dioxolane-2′,3,20-trione, a compound of claim 1.

10. 21-Acetoxy-9α-fluoro-11β-hydroxy-1,4-pregnadieno[16α,17α-d]-[1,3]dioxolane-2′,3,20-trione, a compound of claim 1.

11. A pharmaceutical composition comprising an antiinflammatorily effective amount of a compound of claim 1 and a pharmaceutically acceptable carrier.

12. A pharmaceutical composition of claim 11 wherein the carrier is adapted for topical administration.

13. A pharmaceutical composition of claim 11 containing 1 or 2 antiinflammatorily active ingredients.

14. A method of treating inflammation in a patient in need of such treatment comprising administering to the patient an antiinflammatorily effective amount of a compound of claim 1.

* * * * *